Figure 1:
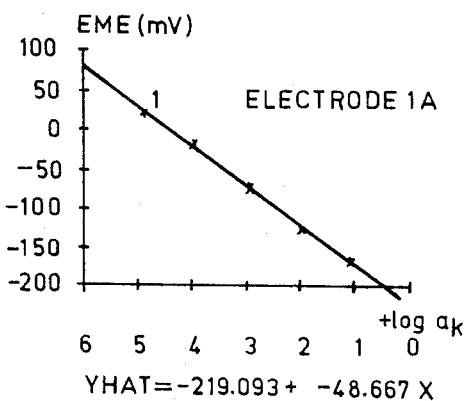
Figure 1:
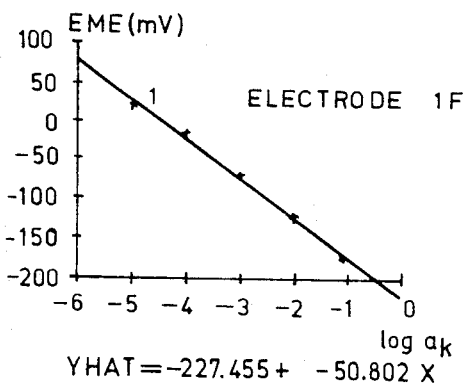
Figure 1:
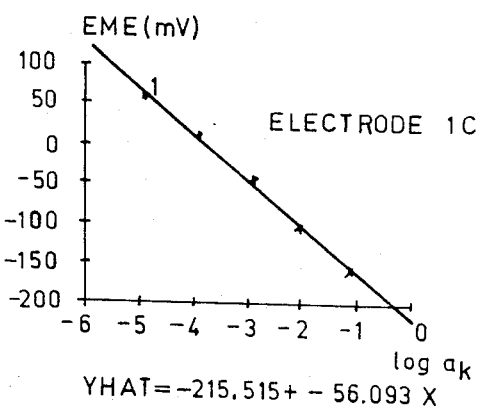

United States Patent [19]

Töke et al.

[11] Patent Number: 4,531,007
[45] Date of Patent: Jul. 23, 1985

[54] CROWN ETHER COMPOUNDS, PROCESS FOR THE PREPARATION OF THE CROWN ETHER COMPLEX FORMING AGENTS AND ION-SELECTIVE MEMBRANE ELECTRODES CONTAINING THE SAME

[75] Inventors: László Töke; Béla Ágai; István Bitter; Erno Pungor; Klára Szepesváry née Tóth; Erno Lindner; Mária Horváth; Jeno Havas, all of Budapest, Hungary

[73] Assignee: Magyar Tudományos Akadémia, Budapest, Hungary

[21] Appl. No.: 486,285

[22] PCT Filed: Jul. 9, 1982

[86] PCT No.: PCT/HU82/00034
§ 371 Date: Mar. 7, 1983
§ 102(e) Date: Mar. 7, 1983

[87] PCT Pub. No.: WO83/00149
PCT Pub. Date: Jan. 20, 1983

[30] Foreign Application Priority Data

Jul. 9, 1981 [HU] Hungary ................. 1999

[51] Int. Cl.³ ............... C07D 405/02; C07D 407/02; C07D 323/00
[52] U.S. Cl. .................. 549/351; 546/270; 521/27
[58] Field of Search .......... 549/351; 546/270

[56] References Cited
PUBLICATIONS

K. Kimura et al., J. Electroanal. Chem., 95, (1979), pp. 91–101.
H. Tamura et al., Bull. Chem. Soc. Japan, vol. 53, (1980), pp. 547–548.
R. M. Izatt et al., Progress in Macrocyclic Chemistry, vol. 2, (1981), pp. 104–109.

*Primary Examiner*—Norma S. Milestone
*Attorney, Agent, or Firm*—Gabriel P. Katona

[57] ABSTRACT

New crown ether derivatives of formula (I)

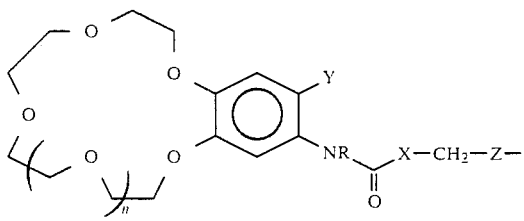

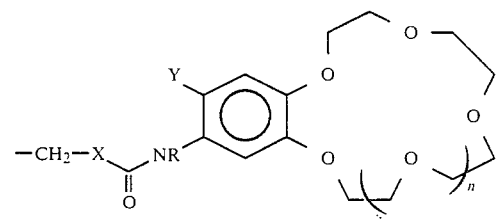

wherein
R stands for hydrogen or $C_{1-4}$ alkyl
n stands for 1,2,
X stands for oxygen, sulphur or a NH-group
Y represents hydrogen or nitro
Z represents a chemical bond, —CH$_2$—, —(CH$_2$)$_{2-4}$—, —CH$_2$OCH$_2$—, —CH$_2$SCH$_2$—,

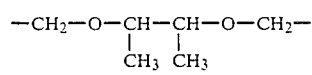

or a group of the formula (1)     (2)

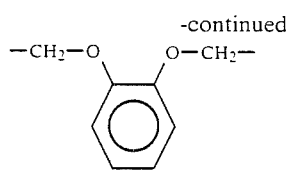
(3)
suitable for forming cation complexes, process for the preparation thereof and alkali or alkali earth metal ion-selective membrane electrodes containing said compounds are described.
3 Claims, 2 Drawing Figures

CROWN ETHER COMPOUNDS, PROCESS FOR THE PREPARATION OF THE CROWN ETHER COMPLEX FORMING AGENTS AND ION-SELECTIVE MEMBRANE ELECTRODES CONTAINING THE SAME

TECHNICAL FIELD

The present invention relates to new crown ether derivatives suitable for forming cation complexes, to a process for the preparation thereof and ion selective membrane electrodes containing said compounds.

BACKGROUND ART

Crown ethers are widely used because of their capability of complexing various cations. The extent of complex formation, complex stability constant, in case of a given cation depends apart from the geometrical characteristics of the crown ether, such as ring-member number, hetero atom number, on the solvent as well. The stoechiometry of the formed complex is influenced by the ratio of the diameter of the crown ether ring and the diameter of the cation. All the above factors justify the use of crown ethers as active ingredient of ion selective membrane-electrodes.

In the last 17 years various substances, inorganic precipitates, various ion exchanging compounds, electrically charged or not charged complex forming agents were used as ion-selective electrodes for measuring various anions (halides, pseudohalides, nitrates etc.) as well as various cations (alkali metal ions, alkali earth metal ions and some heavy metal ions etc.) (Karl Camman, Das Arbeiten mit ionenselektiven Elektroden, Springer Verlag, Berlin, Heidelberg, New York, 1977; Peter L. Bailey, Analysis with Ion-Selective Electrodes, Heyden, London, New York, Rheine, 1976). The various electrodes have different active ingredients, mechanical and dynamical properties and different so called selectivity factors, latter being the most important parameter from the point of view of the use.

In the most significant field of the practical application, i.e. in the field of biochemical applications those electrodes are especially important, which are suitable for monitoring the ionic processes of the cell metabolism in the organism. In case of measuring probes suitable for measuring biologically important ions particularly significant are electrodes suitable for measuring cations, selected from the group of sodium, potassium, calcium and magnesium. Measuring potassium ion is particularly important in life processes. This explains the widely spread research work concentrated on the elaboration of potassium selective electrodes, on the examination of the properties thereof and optimalization of their preparation. The best potassium ion-selective electrode used so far has been the ion-selective electrode having valinomycine as active ingredient (Swiss Patent Specification No. 479,870).

For biological application the most advantageous property of the electrode is its selectivity factor related to sodium ions: $(K_K^{Pot}, Na)$ is about $3 \times 10^{-4}$. When testing the electrode, it could be observed that the valinomycine based potassium electrode has a higher or equal selectivity towards alkali metal ions of great volume ($Rb^+$, $Cs^+$) than towards $K^+$ i.e. the electrode measures said ions better or with nearly same selectivity as potassium. (L. A. R. Pioda, V. Stankova and W. Simon Anal. Letters 2, 1969, 665). As alkali metal ions often occur together in nature, such coincidence of the selectivity factors can be disadvantageous in case of a potassium electrode prepared for other than biochemical purposes.

The above disadvantages can be eliminated without considerable reduction of the selectivity related to the other ions when using bis crown compounds linked by an aliphatic chain as ion selective substance. Kimura et al (Kimura K., Maeda T., Tamura H., Shono T.,: J. Electroanal. Chem. 95, 1979, 91–101, Kimura K., Tamura H., Shono T.: Bull. Chem. Soc. Jpn. 53 547–548, 1980) disclosed two such compound groups and electroanalytical data thereof. These compounds have a common structural element: two benzo-15-crown-5-units, linked up with dicarboxylic acids through oxygen or nitrogen atoms. Practical applicability of these compounds cannot be estimated, as electroanalytical assay of the compounds is not disclosed in the above articles, only selectivity data related to alkali metal ions are included.

DISCLOSURE OF THE INVENTION

We have now found that some bis crown derivatives meet the requirements of the alkali and alkaline earth metal ion selectivity. These compounds bear nitro groups on the aromatic ring of the bis-crown ether structural unit and the chain linking the two crown ether units is attached to the aromatic ring through urethane and urea bond respectively. Said nitro groups form a H-bridge with the N-H unit of the urethane and urea groups resp. intramolecularly. The two crown ether units bring about an optimal steric position necessary to complexing only the K ion and thus a great K selectivity occurs. It is surprising that the selectivity is not dependent upon the quality of the chain binding the crown ether units together (number of heteroatoms, and quality thereof) and on its length.

Many of the new compounds of the invention are suitable for elaborating potassium ion selective electrode. Electrodes prepared from the new compounds show the same potassium ion concentration sensitivity as concentration-sensitivity of the potassium electrode as valinomycine basis, and further its selectivity factor related to alkali metal ions of great volume is better (0.1 to 0.01 than that of the valinomycine based electrode, the selectivity factors of which are in the range from 4.6 to 0.5, at the same time the selectivity factor related to the alkali earth metal ions is the same as that of valinomycine based electrode ($K_{K^+}^{Pot}, Mn^{++} \approx 10^{-4}$).

The new compounds have the general formula:

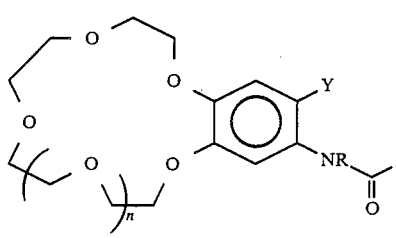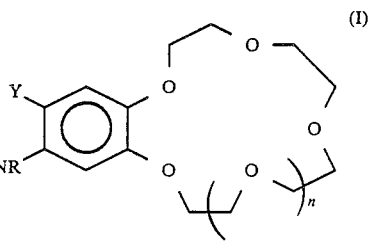

(I)

wherein:
R stands for hydrogen or alkyl containing 1 to 4 carbon atoms;
n is 1, 2;
X stands for oxygen, sulphur or —NH;
Y stands for hydrogen or nitro;
Z represents a chemical bond, —CH$_2$—, —(CH$_2$)$_{2-4}$, —CH$_2$OCH$_2$—, —CH$_2$SCH$_2$—,

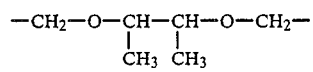

—CH$_2$—O—CH—CH—O—CH$_2$—
                |      |
               CH$_3$  CH$_3$ or a group of the formula:

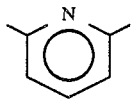 (1)

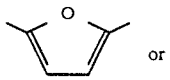 or (2)

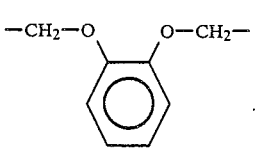 (3)

The compounds of the general formula I may be prepared by:
(a) reacting a compound of the general formula

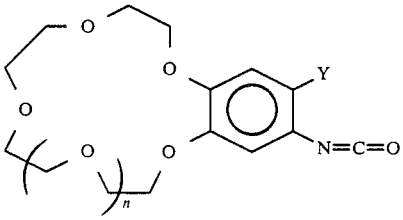

(II)

wherein n and Y are as given above with a compound of the gen. formula:

HX—CH$_2$—Z—CH$_2$—XH     (III)

wherein X and Z are as define above in an organic aprotic solvent. The reaction may be performed at 0°–50° C. in chlorinated hydrocarbons, ethers optionally in the presence of 0.1–0.5 mol% of tertiary amines, such as triethylamine catalyst. The compounds of the formulae II and III are used in a molar ratio of 2:1. The product is isolated by filtration or after removing the solvent by recrystallization from a suitable solvent, such as ethyl acetate or methylisobutyl ketone, or (b) reacting an urethane of the gen. formula:

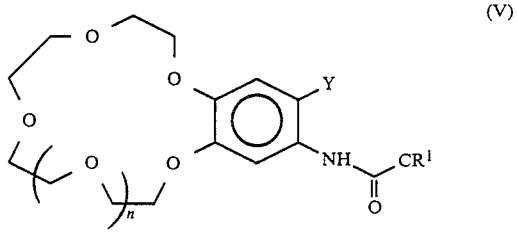

(V)

wherein n and Y are as given above, R$^1$ stands for C$_{1-4}$ alkyl, benzyl, or phenyl- with a compound of the gen. formula

HX—CH$_2$—Z—CH$_2$—XH     (III)

wherein X and Z are as defined above, in an organic aprotic solvent. The reaction may be conducted at 30° to 120° C. in aromatic hydrocarbons, chlorinated hydrocarbons, ethers, optionally in the presence of tertiary amines, such as triethylamine. Compounds of the formulae V and III are used at a molar ratio of 2:1. The product may be isolated by filtration or after removing the solvent by recrystallization from a suitable solvent, preferably from ethyl acetate or methylisobutyl ketone, or (c) reacting an amine of the gen. formula:

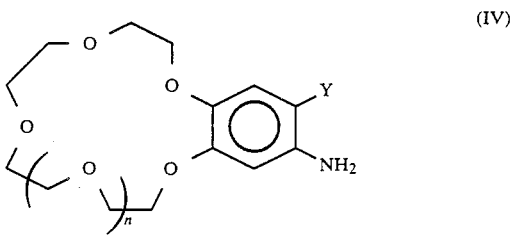

(IV)

wherein n and Y are as defined above with diisocyanates of the gen. formula:

O=C=N—CH$_2$—Z—CH$_2$—N=C=O     (VII)

wherein Z is as given above in an organic aprotic solvent. The reaction may be carried out at 0° to 50° C. in chlorinated hydrocarbons, aromatic hydrocarbons, ethers. The compounds of the formulae IV and VII are used at a molar ratio of 2:1. The product may be isolated by filtration or after removing the solvent by recrystallization from a suitable solvent, preferably from methanol, ethanol, or methylisobutyl ketone, or (d) reacting a compound of the gen. formula:

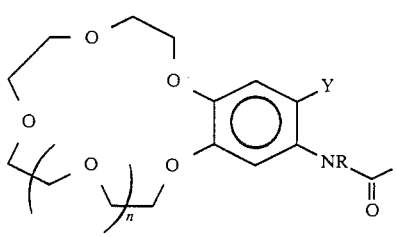 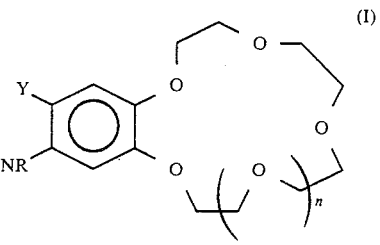

(I)

wherein n, Y and Z are as defined above, X is oxygen or sulphur with amines of the gen. formula:

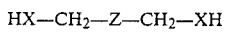

HX—CH₂—Z—CH₂—XH     (III)

wherein Z is as defined above in an organic solvent. The reaction is carried out at 30°-120° C. in aromatic hydrocarbons, chlorinated hydrocarbons, ethers, or alcohols. The compounds of the formulae I and III are used at a molar ratio of 1:1. The product is isolated by filtration or after removing the solvent by recrystallization from a suitable solvent, such as the solvents given above, or (e) by reacting a compound of the gen. formula:

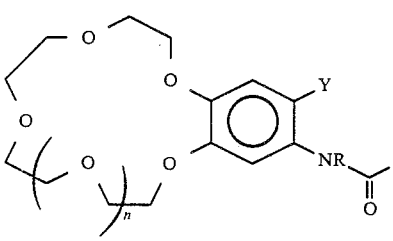 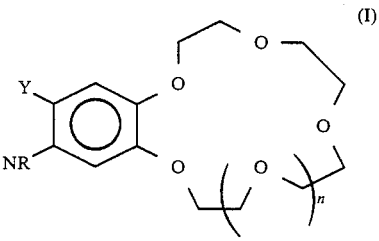

(I)

wherein n, X and Z are as defined above and Y stands for hydrogen, with nitric acid in mineral acids or acetic acid at 30° to 70° C. The product is cooled, filtered or poured on ice followed by extraction with chlorinated hydrocarbons and purified by recrystallization from the above solvents.

Isocyanates of the gen. formula II used as starting materials in process variant (a) have not been disclosed in the technical literature yet. Compounds of the gen. formula II can be prepared by reacting a compound of the gen. formula IV wherein n and y are as defined above with phosgene in an aromatic solvent of high boiling point by methods known per se.

Urethanes of the gen. formula V used as starting materials in process variant (b) are also new. The preparation thereof can be carried out by reacting an amine of the gen. formula IV wherein n and Y are as defined above with a compound of the gen. formula:

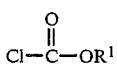

Cl—C—OR¹     (VI)

wherein R¹ is as defined above in an organic aprotic solvent. The reaction is performed at 0°-50° C. in aromatic hydrocarbons, chlorinated hydrocarbons or ethers in the presence of an equivalent amount of tertiary amines, such as triethylamine. The compounds of the gen. formulae IV and VI are used in a molar ratio of 1:1. The product is isolated by filtration or after removing the solvent by recrystallization from a suitable solvent, preferably from an alcohol of the formula R¹OH, ethyl acetate or methylisobutyl ketone. Compounds of the gen. formula IV used as starting materials in process variant (e) are prepared as disclosed in J. Am. Chem. Soc. 98 5198-5202 (1976).

Some of the new compounds according to the invention and a mixture thereof are used as active ingredients of ion selective electrodes as follows:

(a) the selected compound or compounds are built into PVC carrier phase at an amount of 0.2 to 3% by using an appropriate plasticizer such as phtalic acid esters, (b) the selected compound or compounds are built into silicone rubber or into another polymer, such as polyamide, PVC, polyethylene, the dielectrical constant of which is in the range of from 2 to 30, and (c) the selected compound or compounds are applied to a porous membrane dissolved in a suitable solvent, preferably, in the plasticizers mentioned under (a).

The membranes prepared as described above are installed into a suitable electrode and are connected together with the suitable reference electrode for an analytical instrument.

The correlation between cell voltage and logarithm activity ($-\lg a_{K^+} = pK$) is linear in the range of $pK = 1-5.0$ and can be characterized by the so-called modified Nikolsky equation:

$$EME = E_o + S\lg\left(a_i + \sum_{i \neq j} K_{ij}^{pot} a_j^{Z_i/z_j}\right) + E_D$$

wherein:
EME = cell voltage
$E_1$ = constant reference potential independent of the activity of the sample solution
$E_D$ = sum of the diffusion potentials in the cell
$a_i$, $a_j$ activity of the ion to be measured and of the interfering ions
$z_i$, $z_j$ number of charge of the ion to be measured and of the interfering ions
S so-called Nernst factor, the value of which amounts to 59.15 mV/$z_i$ at 25° C.
$K_{ij}$pot selectivity factor

EXAMPLES

Preparation of isocyanates of the gen. formula II 0.1 mole of an amino compound of the gen. formula IV is dissolved in 500 ml chlorobenzene and the solution is added to 150 ml. chlorobenzene saturated with phosgene at room temperature under steady stirring and under introducing phosgene. The reaction mixture is then slowly heated to boiling point. When the evolution of hydrochloric acid gas ceases the introduction of phosgene is interrupted and the excess of phosgene is eliminated under boiling with nitrogen and argon gas (about 1.5-2 hours). Chlorobenzene is distilled off in vacuo. The residue is purified as given in Table I.

The following compounds were prepared as disclosed above:

(IIa) 2-nitro-4,5-(1′,4′,7′,10′,13′-pentacyclopentadeca-2′-ene)phenyl-isocyanate (IIb) 3,4-(1′,4′,7′,10′,13′-pentaoxacyclopentadeca-2′-ene)-phenylisocyanate (IIc) 3,4-(1′,4′,7′,10′,13′,16′-hexaoxacyclooctadeca-2′-ene)phenyl-isocyanate

Preparation of urethanes of the gen. formula V 0.1 mole of an amine of the gen. formula IV is dissolved in 200 ml. of chloroform and to the solution 0.1 mole of chloroformiate of the gen. formula VI is added at room temperature under steady stirring and after 10 minutes 10.1 g of triethylamine are added and the mixture is stirred for further 30-45 minutes. The reaction mixture is then evaporated and the residue is purified as given in Table I.

hydroxy compounds 0.005 mole of triethyl amine catalyst is used.

Isolation (a) if the product precipitates, it is filtered, washed with dioxan or chloroform and recrystallized from the solvent given in Table 2;

(b) if the product is not precipitated, then solvent is distilled off in vacuo and the residue in recrystallized from the solvent given in Table 2.

Process variant (b)

20 moles of an urethane of the formula Va-Vf are dissolved in 50 ml of chloroform (or dioxan, toluene or chlorobenzene) and the solution is stirred for 3-4 hours at 60°-100° C. with 10 moles of α,ω-polymethylene diamine (ethylene diamine 0.6 g., 1,3-propylene diamine 0.74 g., 1,6-hexamethylene diamine 1.16 g.), or with 10 moles of a suitable glycol (ethylene glycol 0.62 g.), diethylene glycol 1.06 g., thiodiethylene glycol 1.22 g., 2,2′-bishydroxyethyl pyrocatechine 1.98 g.) if Y=H and at 30°-80° C. for 0.5-1 hour if Y=NO$_2$. When using hydroxy compounds, 1 drop of triethyl amine catalyst is used and the formed alcohol is eliminated.

Isolation: like in process variant (a).

The so obtained products are identical with the compounds prepared according to process variant (a) (IR, m.p., mixture m.p.)

Yield: 40-90%, if X=NH: 75-90%, if X=O: 40-60%.

Process variant (c)

TABLE 1

Compounds of the gen. formula (II)
Data of the preparation of 4′-isocyanato-benzo-m-crown-n and physical and spectroscopic data thereof

| No. Example | (II) | n | Y | Method of processing | M.p. °C. | Empirical formula molecular weight | | Analysis % calculated | found | IR (cm$^{-1}$) N=C=O | molecular weight M$^x$ (%) |
|---|---|---|---|---|---|---|---|---|---|---|---|
| 1 | a | 1 | NO$_2$ | crystallization benzene-benzine | 116 | C$_{15}$H$_{18}$N$_2$O$_8$ 354.30 | C H N | 50.85 5.12 7.91 | 51.19 4.81 7.81 | 2270 | — |
| 2 | b | 1 | H | vacuo-distillation | 38 a | C$_{15}$H$_{19}$NO$_6$ 309.30 | C H N | 58.24 6.19 4.53 | 57.89 6.59 4.34 | 2300 | 309 (35) |
| 3 | c | 2 | H | vacuo-distillation | | C$_{17}$H$_{23}$NO$_7$ 353.36 | C H N | 57.78 6.56 3.96 | 57.93 6.71 3.89 | 2290 | 353 (3.7) |

(a) m.p.: 150-152° C./0.1 Hgmm
(b) m.p.: 168-180° C./0.1 Hgmm
Yields: a: 94%; b: 70%; c: 74%

Preparation of bis-crown compounds of the gen. formula I

Process variant (a)

A solution of 0.2 mole of isocyanate (formula IIa, b, c) in 500 ml. of absolute dioxan or absolute chloroform is stirred with 0.1 mole of a suitable glycol (ethylene glycol 6.2 g, diethylene glycol 10.6 g thioethylene 12.2 g 2,2′-bis-hydroxyethyl-pyrocatechine 19.8 g., 2,5-dihydroxymethylfuran 12.8 g., 2,6-dihydroxymethylpyridine 13.9 g) or with 0.1 mole of α,ω-polymethylenediamine)ethylene diamine 6.0 g., 1,3-propylenediamine 7.4 g., 1,6-hexamethylene diamine 11.6 g for 1-2 hours at room temperature. When using 5.66 g. (20 moles) of an amine compound of the gen. formula IV (Y=H, n=1) are dissolved in 60 ml of chloroform and the solution is stirred with 1.68 g (10 moles) of hexamethylene diisocyanate for 1 hour at room temperature whereafter the solvent is distilled off. The residue is recrystallized from ethanol. Yield: 6.76 g. (92%), m.p.: 183° C.

Analysis for the formula C$_{36}$H$_{54}$N$_4$O$_{12}$ (734,80): calculated: C 58,84, H 7.41, N 7.63. found: C 58,69, H 7.68, N 7.39.

Product of the formula I wherein Y=H, n=1, Z=(CH$_2$)$_4$—.

Process variant (d)

A solution of 10 moles of a bis-urethane of the gen. formula I (n, Y, Z are as defined above and X=O) in 50 ml of toluene (or chlorobenzene, chloroform or di-n-butyl ether) is stirred together with 10 moles of α,ω-polymethylene diamine (ethylene diamine 0.6 g., 1,3-propylene diamine 0.74 g., 1,6-hexamethylene diamine 1.16 g.) at 80°–110° C. if Y=H and at 60°–80° C. if Y=NO$_2$ for 2–4 hours.

Isolation: as in process variant (a).

Yield: 50–82%.

Products are identical with products obtained in process variants (a) and (b) IR., m.p., mixture m.p., and thin layer chromatogram.

Process variant (e)

10 moles of a bis-crown compound of the gen. formula I (n, X and Z are as defined above, Y=H) are dissolved in 25 ml of chloroform, to the solution 10 ml of acetic acid are added and under steady stirring a solution of 3 ml of 65% nitric acid in 3 ml of acetic acid is added dropwise. The reaction mixture is stirred at room temperature for 10 minutes and at 65° C. for 30 minutes. The mixture is cooled and poured on 50 g of crushed ice, the two layers are separated and the aqueous layer is extracted with 4×20 ml of chloroform. The combined organic layer is washed with 30 ml portions of water. Chloroform is distilled of in vacuo and the residue is recrystallized from the solvent given above. (See Tables).

Yield: 55–78%.

The so obtained nitro derivatives were identical with those obtained according to process variants (a) and (b) IR, m.p., mixture m.p., thin layer chromatogram.

The following compounds were prepared as given above:

(Ia) ethylene-1,2-bis-N-[2'-nitro-4',5'-(1'',4'',7'',10'',13''-pentaoxacyclopentadeca-2''-ene)-phenyl]-carbamate (Ib) ethylene-1,2-bis-N-[3',4'-(1'',4'',7'',10'',13'',16''-hexaoxacyclooctadeca-2''-ene)-phenyl]-carbamate (Ic) diethylether-2,2'-bis-N-[2''-nitro-4'',5''-(1''',4''',7''',10''',13'''-pentaoxacyclopentadeca-2'''-ene)-phenyl]-carbamate (Id) diethylether,2,2'-bis-N-[3'',4''-(1''',4''',7''',10''',13'''-pentaoxacyclopentadeca-2'''-ene)-phenyl]-carbamate (Ie) diethylether-2,2'-bis-N-[3'',4''-(1''',4''',7''',10''',13''',16'''-hexaoxacyclooctadeca-2'''-ene)-phenyl]-carbamate (If) diethylsulphide-2,2'-bis-N-[2''-nitro-4'',5''-(1''',4''',7''',10''',13'''-pentaoxacyclopentadeca-2'''-ene)-phenyl]-carbamate (Ig) diethylsulphide-2,2'-bis-N-[3'',4''-(1''',4''',7''',10''',13''',-pentaoxacyclopentadeca-2'''-ene)-phenyl]-carbamate (Ih) diethylsulphide-2,2'-bis-N-[3'',4''-(1'''4''',7''',10''',13''',16'''-hexaoxacyclooctadeca-2'''-ene)-phenyl]-carbamate (Ii) (1,2-phenylenedioxy)-diethyl-2',2''-bis-N-[3''',4'''-(1'''',4'''',7'''',10'''',13''''-pentaoxycyclopentadeca-2''''-ene)-phenyl]-carbamate (Ij) (1,2-phenylenedioxy)-diethyl-2',2''-bis-N-[3''',4'''1'''',4'''',7'''',10'''',13'''',16''''-hexaoxacyclooctadeca-2''''-ene/-phenyl]-carbamate (Ik) (1,2-phenylenedioxy)-diethyl-2'.2''-bis-N-[2''''-nitro-4'''',5''''-(1'''',4'''',7'''',10'''',13''''-pentaoxacyclopentadeka-2''''-ene)-phenyl]-carbamate (Il) 2,5-bis-[2'-nitro-4',5'-(1'',4'',7'',10'',13''-pentaoxacyclopentadeca-2''-ene)-phenylcarbamoyloxymethyl]-furan.

Yield: 60–85%.

Characteristic data of the products (m.p., recrystallization solvent, IR, $^1$H-NMR, analysis) are in Tables 2–4.

TABLE 2

(I) melting point and analytical, IR spectroscopical data of carbamates of the formula I (X=O)

| No. Example | (I) | n | Y | Z | Op. C.° | Empirical formula molecular-weight | | calculated | found | IR (KBr) cm$^{-1}$ νNH | νN—C—O ‖ O |
|---|---|---|---|---|---|---|---|---|---|---|---|
| 2.1. | a | 1 | NO$_2$ | — | 170–2 (a) | C$_{32}$H$_{42}$N$_4$O$_{18}$ 770.67 | C H N | 49.87 5.49 7.27 | 49.54 5.84 6.96 | 3320 | 1735 |
| 2.2. | b | 2 | H | — | 130–2 (b) | C$_{36}$H$_{52}$N$_2$O$_{16}$ 768.79 | C H N | 56.23 6.82 3.64 | 56.16 7.11 3.45 | 3270 | 1690 |
| 2.3. | c | 1 | NO$_2$ | —CH$_2$OCH$_2$— | 98 (a) | C$_{34}$H$_{46}$N$_4$O$_{19}$ 814.72 | C H N | 50.12 5.69 6.88 | 50.27 5.58 6.72 | 3320 | 1735 |
| 2.4. | d | 1 | H | —CH$_2$OCH$_2$— | 84 (b) | C$_{34}$H$_{48}$N$_2$O$_{15}$ 727.72 | C H N | 56.35 6.68 3.87 | 56.33 7.07 3.95 | 3260 | 1715 1690 |
| 2.5. | e | 2 | H | —CH$_2$OCH$_2$— | 64 (b) | C$_{38}$H$_{56}$N$_2$O$_{17}$ 812.84 | C H N | 56.14 6.94 3.45 | 56.04 7.33 3.44 | 3280 | 1715 1690 |
| 2.6. | f | 1 | NO$_2$ | —CH$_2$SCH$_2$— | 100 (a) | C$_{34}$H$_{46}$N$_4$O$_{18}$S 830.70 | C H N | 49.16 5.58 6.75 | 48.92 5.64 6.15 | 3320 | 1740 |
| 2.7. | g. | 1 | H | —CH$_2$SCH$_2$— | 135 (b) | C$_{34}$H$_{48}$N$_2$O$_{14}$S 740.70 | C H N | 55.13 6.53 3.78 | 55.28 6.96 3.77 | 3280 | 1715 1690 |
| 2.8. | h | 2 | H | —CH$_2$SCH$_2$— | 87 (b) | C$_{38}$H$_{56}$N$_2$O$_{16}$S 728.82 | C H N | 55.06 6.81 3.38 | 54.56 7.30 3.16 | 3270 | 1715 1690 |

Recrystallization:
(a) from ethyl acetate
(b) from methyl-isobutyl-ketone

TABLE 3

Carbamates of the gen. formula I (X=O), (CDCl₃, TMS) PMR spectroscopic data δ/ppm/

| No. Example | (I) | m/n | Y | Z | Ar—H | ring O—CH₂ | |
|---|---|---|---|---|---|---|---|
| 2.1 | a | 15/5 | NO₂ | — | 7.67(s,2H Ar—H—6)<br>8.10(s,2H Ar—H—3) | 3.6–4.4(m.32H), | 4.45(s,4H C(=O)—O—CH₂) |
| 2.2. | b | 18/6 | H | — | 6.77(s,4H Ar—H—5,6)<br>6.98(s,2H Ar—H—3) | 3.5–4.2(m,40H) | 4.37(s,4H C(=O)—O—CH₂) |
| 2.3 | c | 15/5 | NO₂ | —CH₂OCH₂— | 7.58(s,2H Ar—H—3)<br>8.05(s,2H Ar—H—6) | 3.6–4.5(m,40H) | |
| 2.4 | d | 15/5 | H | —CH₂OCH₂— | 6.76(s,4H Ar—H—5,6)<br>7.13(s,2H Ar—H—3) | 3.2–4.5(m,40H) (c) | |
| 2.5. | e | 18/6 | H | —CH₂OCH₂— | 6.82(s,4H Ar—H—5,6)<br>7.10(s,2H Ar—H—3) | 3.5–4.5(m, 48H) | |
| 2.6. | f | 15/5 | NO₂ | —CH₂SCH₂— | 7.61(s,2H Ar—H—3)<br>8.05(s,2H Ar—H—6) | 3.5–4.6(m,ᵃ) | 2.90(t,4H S—CH₂) (d)<br>4.36(t,C(=O)—O—CH₂ (a) |
| 2.7. | g | 15/5 | H | —CH₂SCH₂— | 6.75(s,4H Ar—H—5,6) | 3.5–4.5(m,ᵃ) | 2.83(t,4H S—CH₂<br>4.33(t,C(=O)—O—CH₂ (a) |
| 2.8. | h | 18/6 | H | —CH₂SCH₂— | 6.86(s,4H Ar—H—5,6)<br>7.22(s,2H Ar—H—3) | 3.6–4.5(mᵇ) | 2.88(t,4H S—CH₂)<br>4.38(t, C(=O)—O—CH₂) (b) |

A(a): brutto integral 36H
(b): brutto integral 44H
(c): CH₂ of the chain is indicated by arising from the multiplett at 3.34 and 4.31 ppm.
(d): coupling constant in each case J = 6 Hz 2.9. (Ii)
M.p.: 148–150° C. (EtOH)
Analysis: C₄₀H₅₂N₂O₁₆ (816.8)
calculated:  C: 58.82%;  H: 6.42%;
             N: 3.43%;
found:       C: 58.42%;  H: 6.66%;
             N: 3.17%.

n = 1
Y = H
Z = group of the formula (3)

IR:  νN—C(=O)(—O)  1690 cm⁻¹

(KBr)  νNH  3280 cm⁻¹
PMR    δ(ppm)  660 MHz, CDCl₃, TMS
3.5–4.6  O—CH₂         (m, 40H)
6.76     Ar—H—5,6     (s, 4H)
6.93     Ar—H          (s, 4H)
7.12     Ar—H—3       (s, 2H)

2.10. (Ij)
M.p.: 109° C. (methyl-izobuthyl-ketone)
Analysis: C₄₄H₆₀N₂O₁₈ (904.92)
Calculated:  C: 58.39%;  H: 6.68%;
             N: 3.10%;
found:       C: 58.35%;  H: 7.07%;
             N: 3.27%.

n = 2
Y = H
Z = group of the formula (3)

IR:  νN—C(=O)(—O)  1685 cm⁻¹

(KBr)  νNH  3250 cm⁻¹
PMR    δ(ppm)  (60 MHz, CDCl₃, TMS)
3.4–4.6  O—CH₂         (m, 48H)
6.76     Ar—H—5,6     (s, 4H)
6.92     Ar'—H         (s, 4H)
7.14     Ar—H—3       (s, 2H)

2.11. (Ik)
M.p.: 118–119° C.
Analysis: C₄₀H₅₀N₄O₂₀ (906.8)
calculated:  C: 52.98%;  H: 5.56%;
             N: 6.18%;
found:       C: 52.87%;  H: 5.24%;
             N: 6.55%.

n = 1
Y = NO₂
Z = group of the formula (3)

IR(KBr)  νN—C(=O)(—O)  1735 cm⁻¹

νNH  3300 cm⁻¹

2.12. (Il)
M.p.: 190–192° C. (toluene-benzene)
Analysis: C₃₆H₄₄N₄O₁₉ (836.7)
calculated:  C: 51.67%;  H: 5.26%;
             N: 6.69%;
found:       C: 52.39%;  H: 5.95%;
             N: 6,76%.

n = 1
Y = NO₂
Z = group of the formula (2)

IR(KBr)  νN—C(=O)(—O)  1730 cm⁻¹

νNH  3350 cm⁻¹
PMR  ppm      δ(60 MHz, CDCl₃, TMS)
3.60–4.40   O—CH₂ (m, 32H) ring
5.10        —CH₂—(furane) (s, 4H)
6.39        —CH=(furane) (s, 2H)
7.28        Ar—H—3 (s, 2H)
7.60        NH (2H)
8.05        Ar—H—6 (s, 2H)

TABLE 4

Melting point and analytical and IR spectroscopic data of ureas of the formula (Ia—d)

| No. Example | (I) | Y | Z | M.p. °C. | empirical formula molecular weight | | Analysis (%) calculated | found | $\nu$NH | $\nu$ (cm$^{-1}$) $\nu$N—C(=O)(N) | /shoulder |
|---|---|---|---|---|---|---|---|---|---|---|---|
| 2.13. | p | NO$_2$ | —CH$_2$— | 235 | C$_{33}$H$_{46}$N$_6$O$_{16}$ 782,73 | C H N | 50.64 5.92 10.74 | 50.31 6.23 10.38 | 3370 | 1700 | |
| 2.14. | q | H | —(CH$_2$)$_4$— | 183 | C$_{33}$H$_{48}$N$_4$O$_{12}$ 692,66 | C H N | 57.21 6.89 8.09 | 56.64 7.27 7.67 | 3280 broad | 1620 | 1660 |
| 2.15. | r | NO$_2$ | —(CH$_2$)$_4$— | 230 | C$_{36}$H$_{52}$N$_6$O$_{16}$ 824,80 | C H N | 52.42 6.36 10.19 | 52.50 6.44 9.70 | 3370 | 1690 | |
| 2.16. | s | H | —(CH$_2$)$_4$— | 183 | C$_{36}$H$_{54}$N$_4$O$_{12}$ 734,80 | C H N | 58.84 7.41 7.63 | 58.69 7.68 7.39 | 3280 broad | 1630 | 1680 |
| 2.17. | t | NO$_2$ | —(CH$_2$OCH$_2$)$_2$ | 153 | C$_{36}$H$_{52}$N$_6$O$_{18}$ 856,83 | C H N | 50.46 6.12 9.81 | 50.31 6.26 9.74 | 3380 3300 | 1690 | |

TABLE 5

Characteristic data of urethanes of the gen. formula (V)

| (V) | n | Y | R$^1$ | m.p. (°C.) | empirical formula molecular weight | | Analysis calculated | found | IR (KBr) | Yield % |
|---|---|---|---|---|---|---|---|---|---|---|
| a | 1 | NO$_2$ | Me | 147 (MeOH) | C$_{16}$H$_{22}$N$_2$O$_9$ 386.34 | C H N | 49.74 5.74 7.25 | 50.47 5.76 6.85 | 1740/1725 | 82 |
| b | 1 | H | Me | 128 (MeOH) | C$_{16}$H$_{23}$NO$_7$ 341.34 | C H N | 56.30 6.79 4.10 | 56.37 8.59 4.13 | 1720/1700 | 78 |
| c | 2 | H | Me | 83 (MeOH) | C$_{18}$H$_{27}$NO$_8$ 385.40 | C H N | 56.09 7.06 3.63 | 56.03 7.44 3.61 | 1720/1700 | 76 |
| d | 1 | NO$_2$ | i-Pr | 138 (i-Pr—OH) | C$_{18}$H$_{28}$N$_2$O$_9$ 414.39 | C H N | 52.16 6.32 5.76 | 51.35 6.30 6.14 | 1720 | 87 |
| e | 1 | H | i-Pr | 139 (i-Pr—OH) | C$_{18}$H$_{27}$NO$_7$ 369.39 | C H N | 58.52 7.36 3.79 | 57.44 7.25 3.96 | 1700/1685 | 83 |
| f | 2 | H | i-Pr | 104 (i-Pr—OH) | C$_{20}$H$_{31}$NO$_8$ 413.45 | C H N | 58.09 7.56 3.39 | 57.44 7.25 3.34 | 1690 | 79 |

3. Preparation of potassium ion-selective membrane by using crown compounds of the gen. formula (I) 3.1 20–60, preferably about 35 parts by weight of PVC powder (e.g. SDP Hochmolekular, Lonza A.G., Basel, Switzerland) are dissolved in about 2–3 ml of tetrahydrofuran, and this solution is poured into a vessel containing 0.2–10 mg. preferably 1–5 parts by weight of active ingredient (i.e. a member of the group of the compounds of the gen. formula I or a mixture of some members) and 60–120 mg preferably about 65 parts by weight of a so called plasticizer (an organic solvent of a dielectrical constant of 2–30, such as phtalic acid ester or sebacic acid ester). The mixture is shaken until a homogenity is achieved.

On a glass plate of flat surface a glass ring of an height of 10 mm and diameter of 25–35 mm is fixed by means of a rubber ring whereafter 3 ml of the prepared mixture is poured on the glass ring and covered with a filter paper. Tetrahydrofuran evaporates at room temperature within 1–2 days through the filter paper and at the bottom of the glass ring an elastic membrane of 0.1–0.5 mm thickness remains as a residue which can be collected readily from the glass plate.

3.2. 2–10 mg, preferably 1–10 parts by weight of active ingredient and 50–200 mg preferably 90–99 parts by weight of dimethyl polysiloxane (e.g. Silopren K 18000, Farbenfabrik Bayer) are dissolved in about 2–4 ml of carbon tetrachloride. To the solution a crosslinking agent in appropriate amount is added. Every catalyst curing cold suitable for cross-linking, such as T-37 (Wacker Chemie GmbH, Munchen) can be used and the mixture is then poured into the glass ring fixed on the glass plate described in 3.1 and one may further proceed as disclosed in 3.1.

3.3. 2–10 mg. preferably 1–10 parts by weight of active ingredient are pulverized in an achate mortar and dispersed in 50–20 mg preferably 90–99 parts by weight of dimethylpolysiloxane (e.g. Silapren K-1000, Farbenfabrik Bayer) until a statistically homogeneous suspension is obtained. Cross-linking agent is added in an amount necessary to curing (e.g. 1 part by weight of dibutyl-Sn-dilaurate and 2 parts by weight of hexaethoxy siloxane) whereafter the mixture is applied to a plastic plate at an equal extent in a thickness of 0.01–1 mm. After curing, what takes at most a few hours, the elastic plate can be collected from the plastic plate.

3.4. 1–20 parts by weight of active ingredient are dissolved in water immiscible solvent (dielectrical constant of which is 2–30) such as phtalic acid esters, sebacic acid esters, o-nitrophenyl-octyl ether and a porous membrane is wet with the thus obtained solution.

3.5. The tetrahydrofuran solution prepared according to 3.1 containing plasticizer and active ingredient or a carbon tetrachloride dimethylpolysiloxane solution prepared according to 3.2 containing active ingredient and catalyst or a dimethylpolysiloxane active ingredient suspension prepared according to 3.3 containing crosslinking agent and/or a catalyst is applied to an electrone-conducting substance, preferably metal silver, silver, silver chloride wire, platinum or gold fibre, graphite rod etc.

4. Electrochemical properties of some selected active ingredients of the gen formula I used as potassium ion selective membrane electrode.

A PVC carrier phase membrane was prepared according to Example 3.1 from the selected active ingredient such as Ia, Ic, Id, If, Ip, wherafter it was built into a suitable electrode body (such as Philips IS-561 liquid membrane electrode body) and the following measuring cell was formed:

$$\underbrace{Ag, AgCl|0.01\ M\ KCl|ion\text{-}selective|sample\ solution|}_{\text{ion-selective electrode}}\ \text{membrane}$$

$$\underbrace{|0.1\ M\ LiOOCCH_3\ ||\ 0.1\ M\ KCl|Ag, AgCl}_{\text{double junction reference electrode}}$$

Figure 2:
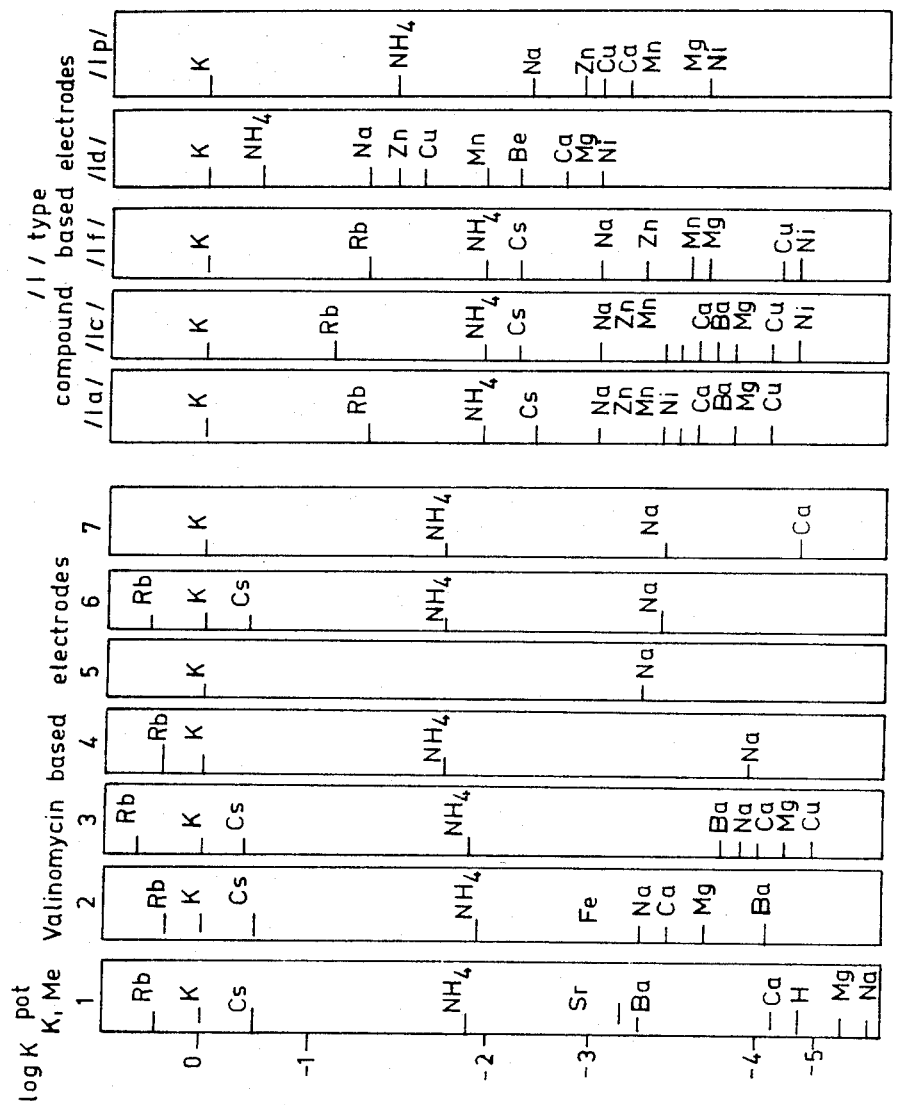

EME$-$lg $a_{K^+}$ calibration curves were plotted in the range of $10^{-1}$M KCl–$10^{-6}$M KCl using the potential data measured with the above measuring cell shown in FIG. 1 when using as active ingredients Ia, Ic, If. The selectivity factors of the electrodes were determined by the so called separate solution method (Moody, G. J., Thomas, J. D. R.: Selective Ion-Sensitive Electrodes, Watford, Merrow Publishing Co. Ltd., England 1971) by using solutions of concentration of $10^{-1}$M. In FIG. 2 selectivity factors of the potassium selective electrode related to various ions are shown for the sake of comparison for both valinomycine-based electrode and for the electrode containing as active ingredient the new compound of the gen. formula I of the invention. When comparing selectivity data of the electrodes prepared similarly by using substances Ic and Id respectively the complex conformation fixing role of the nitro group is proved i.e. this property is critical for influencing ion selectivity.

We claim:

1. Crown compound of the formula

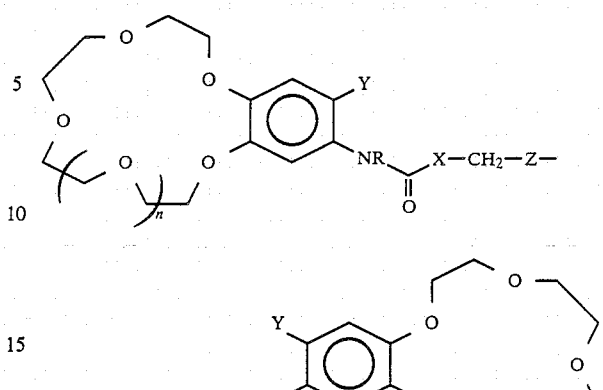

wherein
R stands for hydrogen or $C_{1-4}$ alkyl,
n stands for 1, 2,
X stands for oxygen,
Y represents hydrogen or nitro,
Z represents a chemical bond, —CH$_2$OCH$_2$—, —CH$_2$SCH$_2$—,

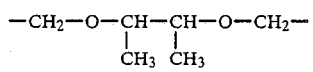

or a group of the formula

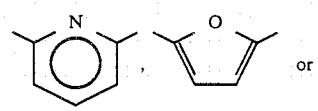, 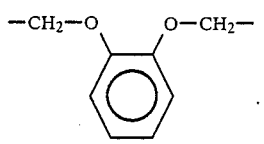

2. The compound of claim 1, which is ethylene-1,2-bis-N-[2'-nitro-4',5'-(1″,4″,7″,10″,13″-pentaoxacyclopentadeca-2″-ene)-phenyl]-carbamate.

3. A crown compound according to claim 1, wherein the compound is diethylsulfide-2,2'-bis-N-[2″nitro-4″,5″-(1‴,4‴,7‴,10‴,13‴-pentaoxacyclopentadeca-2‴-ene)-phenyl]-carbamate.

* * * * *